United States Patent [19]

DeLuca et al.

[11] Patent Number: 5,089,641
[45] Date of Patent: Feb. 18, 1992

[54] SYNTHESIS OF 1α-HYDROXY-SECOSTEROL COMPOUNDS

[75] Inventors: Hector F. DeLuca, Deerfield; Heinrich K. Schnoes; Kato L. Perlman, both of Madison, all of Wis.

[73] Assignee: Wisconsin Alumni Research Foundation, Madison, Wis.

[21] Appl. No.: 667,440

[22] Filed: Mar. 11, 1991

[51] Int. Cl.$^5$ .............................................. C07C 75/00
[52] U.S. Cl. ................................................... 552/653
[58] Field of Search ........................................ 552/653

[56] References Cited

PUBLICATIONS

Kutner, A., et al., "Novel Convergent Synthesis of Side-Chain-Modified Analogues of 1α,25-Dihydroxycholecalciferol and 1α,25-Dihydroxyergocalciferol", *J. Org. Chem.* 53, pp. 3450-3457 (1988).

Andrews, D. "Synthesis of 25-Hydroxy-and 1α,2-5-Dihydroxyvitamin $D_3$ from Vitamin $D_2$ (Calciferol)", *Journal of Organic Chemistry*, 51, pp. 4819-4828 (1986).

*Primary Examiner*—Howard T. Mars
*Assistant Examiner*—Kimberly J. Kestler
*Attorney, Agent, or Firm*—Andrus, Sceales, Starke & Sawall

[57] ABSTRACT

This invention provides a new method of making secosterol compounds, and in particular to the preparation of 1α-hydroxy-homopregnacalciferol which is a secosterol compound that is effective in inducing the differentiation of malignant cells and is therefore useful for the treatment of malignancies such as leukemia.

13 Claims, No Drawings

SYNTHESIS OF 1α-HYDROXY-SECOSTEROL COMPOUNDS

This invention was made in the course of research supported by the U. S. Government under a grant from the Public Health Service. The Government has certain rights to this invention.

TECHNICAL FIELD

This invention relates to secosterol compounds, an in particular, 1α-hydroxy-homopregnacalciferol which is a secosterol compound that is effective in inducing the differentiation of malignant cells, and finds use for the treatment of malignancies such as leukemia. More specifically, this invention relates to a novel preparation of secosterol compounds, and in particular to the preparation of 1α-hydroxy-homopregnacalciferol.

BACKGROUND OF THE INVENTION

A useful therapeutic method for the treatment of malignancies is the administration of compounds that stimulate the differentiation of malignant cells to normal cells, thereby inhibiting and/or reversing the malignant transformation. Thus, it has been shown by Suda et al (U. S. Pat. No. 4,391,802) that 1α-hydroxyvitamin D compounds (e.g. specifically 1α,25-dihydroxyvitamin $D_3$ and 1α-hydroxyvitamin $D_3$) possess, for example, potent antileukemic activity by virtue of inducing the differentiation of malignant cells (specifically leukemia cells) to non-malignant macrophages (monocytes). Hence, these compounds are useful for the treatment of certain malignancies, and specifically for the treatment of leukemia (Suda et al., U.S. Pat. No. 4,391,802). When used for such treatment, however, these known 1α-hydroxyvitamin D compounds have the disadvantage that they are also very potent calcemic agents, i.e. they cause elevated blood calcium levels by stimulating intestinal calcium absorption and bone calcium resorption. This calcemic activity represents the well known classical function of these compounds. Furthermore, the cell differentiation activity (and, hence, anti-leukemic activity) of these compounds correlates with their calcemic activity. For example, 1, 25-dihydroxyvitamin $D_3$, the most potent compound in inducing the differentiation of malignant cells to macrophages, is also the most potent vitamin D metabolite in stimulating calcium transport or raising serum calcium levels. For practical use a cell-differentiating agents, this potent calcemic activity is, of course, an undesired side effect, since the doses required for efficacy in differentiating malignant cells can lead to excessively high and non-physiological serum calcium levels in the treated subjects.

A novel class of secosterol compounds has also been prepared (U.S. Pat. No. 4,940,700) which exhibit high differentiation activity towards malignant cells, such as leukemia cells, but do not have the undesired side effects (potent calcemic action) of some of the known compounds mentioned above. This selectivity and specificity of action makes the secosterols useful and preferred agents for the treatment of malignancies such as leukemia.

This class of secosterols is characterized by the general structures I and II shown below:

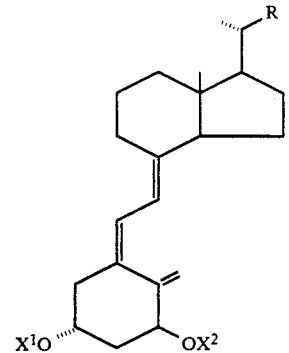

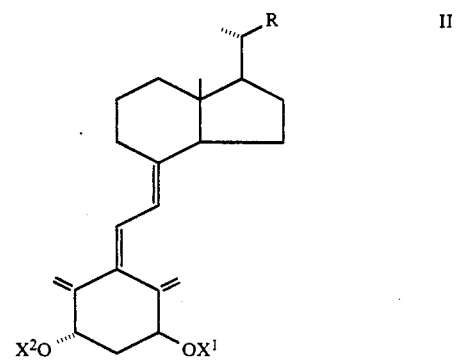

where R is methyl, ethyl or propyl and where each of $X^1$ and $X^2$ represent, independently, hydrogen or an acyl group.

Purely structurally, this class of secosterols has similarity with some of the known vitamin D compounds. Unlike the known vitamin D compounds, however, the secosterols do not express the classic vitamin D activities in vivo, i.e. stimulation of intestinal calcium transport, or the mobilization of bone calcium, and hence they cannot be classified as vitamin D derivatives from the functional point of view. These secosterols are remarkably effective in inducing the differentiation of leukemia cells to normal (non-malignant) macrophages, since, as mentioned above, potent cell differentiation activity among the known vitamin D-related compounds was always closely correlated with potent calcemic activity. Thus, the secosterols overcome the shortcomings of the known vitamin D-related antileukemic agents mentioned above, and can be considered preferred agents for the control and treatment of malignant diseases such as leukemia. This finding provides an effective method for the treatment of malignancies, since the above described secosterols, and preferably 1α-hydroxy-homopregnacalciferol, i.e. the secosterol of general structure I where R is methyl and $X_1$ and $X_2$ are both hydrogen, can be administered to subjects in doses sufficient to cause differentiation of malignant cells to normal cells, without producing simultaneously unphysiologically high and deleterious blood calcium levels.

A related substance, 1α-hydroxypregnacalciferol, has been prepared by Lam et al. [Steroids 26, 422 (2975)]. It should be noted that in addition to the novel synthesis disclosed herein, the secosterols of structures I and II, where R is methyl, ethyl or propyl, can also be prepared according to the general process illustrated in U.S. Pat. No. 4,940,700. Suitable starting materials for the process disclosed in U.S. Pat. No. 4,940,700 are i-ether steroids where, depending on the final product desired, R may be methyl, ethyl or propyl.

DISCLOSURE OF THE INVENTION

The present invention provides an improved and novel synthesis of secosterol compounds defined by structures I and II above. Although the specific example disclosed herein illustrates the synthesis of 1α-hydroxy-homopregnacalciferol, the method disclosed herein is to be considered general in nature and appropriate for synthesizing any of the secosterols defined herein. In general, the method of the present invention utilizes the reagents and conditions illustrated in Scheme I and comprises tosylating the appropriate alcohol and thereafter reducing the tosyl derivative to the desired 22-alkyl compound. The 22-alkyl compound may then be deprotected to provide the desired secosterol, namely, 1α-hydroxy-22-methyl-pregnacalciferol (commonly referred to as 1α-hydroxy-homopregnacalciferol) where R is methyl and $X^1$ and $X^2$ are both hydrogen, 1α-hydroxy-22-ethyl-pregnacalciferol where R is ethyl and $X^1$ and $X^2$ are both hydrogen, and 1α-hydroxy-22-propyl-pregnacalciferol where R is propyl and $X^1$ and $X^2$ are both hydrogen.

The method of making these secosterols may be broadly represented as follows wherein the method comprises the steps of providing a tosylate of the formula

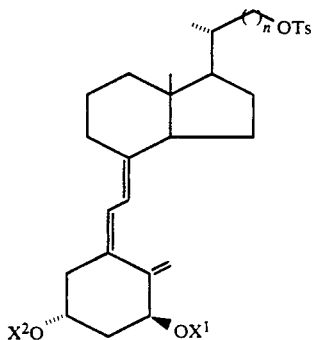

where n represents an integer being a value of 1 to 3, and $X^1$ and $X^2$ represent, independently, a hydroxy-protecting group, reducing the tosylate to a 22-alkyl derivative of the formula

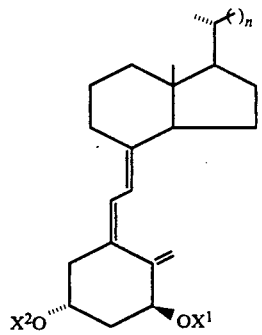

where n, $X^1$ and $X^2$ are as defined above, and thereafter converting the 22-alkyl derivative to the desired 1α-hydroxy-pregnacalciferol (depending upon the value of n) wherein $X^1$ and $X^2$ are both hydrogen.

More specifically, the present invention provides an improved and novel synthesis of 1α-hydroxy-homopregnacalciferol (synthesized earlier in U.S. Pat. No. 4,940,700), and involves a methodology similar to that provided for synthesizing side chain modified analogues of 1,25-dihydroxycholecalciferol as shown in Kutner et al, J. Org. Chem., 1988, 53, 3450. Thus, compound (6) illustrated in Process Scheme I herein, namely, (5Z,7E)-(1S, 3R, 20S)-1,3-Bis (tert-butyldimethylsilyl)-oxy-9,10-seco-22,23-dinor-5,7,10 (19)-cholatrienol 22-p-toluenesulfonate, has previously been synthesized according to that published procedure. The key step herein, however, is the reduction of the 22-tosyl derivative (6) to the 22-methyl compound (18), i.e. step XII in Process Scheme I disclosed herein. This is accomplished by the nucleophilic displacement of the tosylate (6) with $LiAlH_4$ to give the protected homopregnacalciferol (18). Compound (18) in turn is then deprotected with tetrabutyl ammonium fluoride in THF to give compound (19), namely, 1α-hydroxy-homopregnacalciferol.

As used in this description and the claims, an acyl group is an alkanoyl group of 1 to 6 carbons in all its isomeric forms, or an aroyl group, such as benzoyl, or halo-, nitro- or alkyl-substituted benzoyl groups, or a dicarboxylic acyl group such as oxalyl, malonyl, succinoyl, glutaroyl, or adipoyl. "Alkyl" represents a straight-chain or branched hydrocarbon radical of 1 to 5 carbons in all its isomeric forms, such as methyl, ethyl, propyl, isopropyl, butyl, isobutyl, pentyl, etc. The term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings.

Preparation of 1α-Hydroxy-Homopregnaciferol

3β-Hydroxy-22,23-dinor-5,7-choladienic Acid Methyl Ester (10). Alkaline hydrolysis of the 3β-acetoxy group of 8 followed by esterification of the carboxylic group and protection of the 3β-hydroxyl with tert-butyldimethylsilyl chloride afforded ester 9 in 72% yield. A mixture of 1.0 g (2.1 mmol) of 9, 0.42 g (1.5 mmol) of dibromantin, and 0.91 g (10 mmol) of anhydrous sodium bicarbonate in 20 mL of hexane was heated under reflux in a nitrogen atmosphere for 30 min until no 9 was detected (TLC, hexane/ethyl acetate, 3:1). The precipitate was filtered off and the solution dried down under reduced pressure. To the solution of the residue in 5 mL of anhydrous THF was added 0.06 g (0.19 mmol) of tetrabutylammonium bromide, and the mixture was stirred at room temperature for 30 min. under nitrogen. A solution of tetrabutylammonium fluoride (10 mL, 1M in THF) was then added followed by 0.7mL of s-collidine and the mixture was stirred under nitrogen at room temperature for 1 h. Another 5 mL of tetrabutylammonium fluoride solution was added and stirring was continued for 3 h. To the reaction mixture was added 50 mL of ether, and the organic phase was washed with water, cold 1 N hydrochloric acid, and 10% sodium bicarbonate, and dried ($MgSO_4$). Chromatography on 70–230-mesh silica gel (30g) with 10% ethyl acetate in hexane gave ester 10 (0.44 g 58%) as a colorless oil. An analytical sample was obtained by HPLC (system A, $R_v$ 77 mL): IR (film) 1737, 1604, 1495, 1082, 1030 cm$^{-1}$; UV (3% 2-propanol in hexane) $\lambda_{max}$ 262 nm ($\delta$7000), 272 nm (9800), 282 (10500), 293 (6000; $^1$H NMR (CDCl$_3$)$\delta$ 0.54 (3H, s, 18-CH$_3$), 0.94 (3H, s, 19-CH$_3$), 1.22 (3 H, d, J=6Hz, 21-CH$_3$), 3.6 (1 H, m, 3-H), 3.68 (3H, s, CO$_2$CH$_3$), 5.42 (1 H, m, 6-H), 5.58 (1 H, m, 7-H); MS, m/z (relative intensity) 358 (61), 340 (12), 325 (100), 299 (68), 271 (7), 253 (17), 237 (26), 211 (27), 143 (72), 119 (35).

2. (5Z,7E)-(3S.20S)-3-Hydroxy-9,10-seco-5,7,10(19)-pregnatriene-20-carboxvlic Acid Methyl Ester (11). A solution of 830 mg (2.3 mmol) of diene 10 in 350 mL of 1:4 (v/v) benzene-ethyl ether was irradiated with stirring under nitrogen in a water-cooled quartz immersion well equipped with a Vycor filter using Hanovia 608A36 medium-pressure UV lamp for 40 min. (4 × 10 min). The reaction was monitored by HPLC using 2% 2-propanol in hexane at 25 nm. The solution was dried down under reduced pressure, redissolved in 100 mL of absolute ethanol, and heated under reflux in a nitrogen atmosphere for 3 h. Then the solution was concentrated, redissolved in 1 mL of 10% ethyl acetate in hexane, and chromatographed on 70–230-mesh silica gel (30 g). Ester 11 (298 mg, 36%) was eluted by using a mixture of 15% ethyl acetate in hexane. An analytical sample was obtained by HPLC (Zorbax silica, Phenomenex-solvent system, 2% 2-propanol in hexane): IR (film) 1738 cm$^{-1}$; UV (EtOH) $\lambda_{max}$ 264 nm, $\lambda_{min}$ 228 nm; $^1$H NMR (CDCl$_3$) $\lambda$ 0.56 (3 H, s, 18-CH$_3$), 1.20 (3 H, d, J = 7 Hz, 21-CH$_3$), 3.66 (3 H, s, CO$_2$CH$_3$), 3.95 (1 H, m, 3-H), 4.80 (1 H, d, J = 1.2 Hz, 19Z-H), 5.05 (1 H, d, J = 1.2 Hz, 19 E-H), 6.03 (1 H, d, J = 11 Hz, 7-H), 6.23 (1 H, d, J = 11 Hz, 6-H); MS, m/z (relative intensity) 358 (M+, 45), 340 (9), 325 (45), 299 (22), 253 (19), 237 (18), 136 (60), 118 (100).

3. (7E)-(3R,5R,6R,20S)-6-Methoxy-3,5-cyclo-9,10-seco-7,10-(19) -pregnadiene-20-carboxylic Acid Methyl Ester (13). Ester 11 was converted into tosylate 12 by the known method using p-toluenesulfonyl chloride in pyridine at 4° C. for 20 h. A solution of 102 mg (0.2 mmol) of 12 in 2 mL of anhydrous dichloromethane was added to a solution of 250 mg of anhydrous potassium bicarbonate in 15 mL of methanol with stirring at 55° C. The mixture was stirred under nitrogen for 24 h at 55° C. The solvents were then removed under reduced pressure and the residue extracted with ether. The organic phase was washed with water and dried (MgSO$_4$). Silica gel chromatography, using 20% ethyl acetate in hexane, gave 13 (50 mg, 68%) as a colorless oil; $^1$H NMR (CDCl$_3$) $\delta$ 0.54 (3H, s, 18-CH$_3$), 0.74 (1 H, m, 3-H), 0.91 (1 H, m, 4-H), 1.20 (3 H, d, J = 7 Hz, 21-CH$_3$), 3.25 (3H, s, 6R-OCH$_3$), 3.65 (3H, s, 22-CO$_2$CH$_3$), 4.15 (1 H, d, J = 9 Hz, 6-H), 4.88 (1 H, br s, 19Z-H), 5.00 (1 H, d, J = 9 Hz, 7-H), 5.02 (1 H, br s, 19E-H); MS, m/z (relative intensity) 372 (M+, 17), 340 (100), 253 (48), 221 (40), 135 (72).

4. (5Z, 7E)-and (5E,7E)-(1S,3R,20S)-1-Hydroxy-3-acetoxy-9,10-seco-5,7,10 (19)-pregnatriene-20-carboxylic Acid Methyl Esters (15 and 16). tert-Butyl hydroperoxide (112 $\mu$L, 3.0 M in toluene) was added to a suspension of 9 mg (0.8 mmol) of selenium dioxide in 2 mL of dry dichloromethane. The mixture was stirred at room temperature under nitrogen until a clear solution was formed. Anhydrous pyridine (12 $\mu$L, 0.15 mmol) was then added followed by a solution of 50 mg of ester 13 in 2 mL of dichloromethane The mixture was stirred under nitrogen for 30 min. Cold 10% sodium bicarbonate (2 mL) was added and the mixture extracted with ether. The organic phase was washed with cold 10% sodium bicarbonate and ice water and dried over anhydrous MgSO$_4$. Silica gel chromatography (10–20% ethyl acetate hexane) afforded 12.5 mg of alcohol 14. The product was then immediately dissolved in 0.5 mL of glacial acetic acid and the solution was heated at 55° C. with stirring under nitrogen for 15 min. The reaction mixture was poured over ice, extracted with ether, and washed with ice-cold saturated sodium bicarbonate. The combined ether extracts were washed with water and dried (MgSO$_4$). Analytical samples of 5Z,7E and 5E,7E isomers, 15 and 16, respectively, were obtained by preparative HPLC in a ratio of 2.5:1. Isomers 15 and 16 were separated by the maleic anhydride procedure to give 6 mg of 15 (20% overall yield from 12).

15: HPLC, R$_v$ 68 mL; UV (EtOH) $\lambda_{max}$ 264 nm, $\lambda_{min}$ 227, A264/A227 = 2.07; $^1$H NMR (CDCl$_3$) $\delta$0.56 (3 H, s, 8-CH$_3$), 1.20 (3 H, d, J = 6.5 Hz, 21-CH$_3$), 2.04 (3 H, s, 3$\beta$-acetyl), 3.66 (3 H, s, 22-CO$_2$CH$_3$), 4.4 (1 H, m, 1-H), 5.2 (1 H, m, 3-H), 5.01 (1 H, br s, 19E-H), 5.34 (1 H, br s, 19Z-H), 6.01 (1 H, d, J = 10 Hz, 7-H), 6.33 (1 H, d, J = 10 Hz, 6-H); MS, m/z (relative intensity), 416 (M+, 4), 356 (100), 338 (21), 251 (13), 134 (95).

16: HPLC, R$_v$ 78 mL; UV (EtOH) $\lambda_{max}$ 267 nm, $\lambda_{min}$ 227, A267/A227 = 3.51; $^1$H NMR (CDCl$_3$) $\delta$0.56 (3 H, s, 8-CH$_3$), 1.20 (3 H, d, J = 6.5 Hz, 21-CH$_3$), 2.04 (3 H, s, 3$\beta$-OAc), 3.66 (3 H, s, 22-CO$_2$CH$_3$), 4.5 (1 H, m, 1-H), 5.3 (1 H, m, 3-H), 4.99 (1 H, br s, 19E-H), 5.13 (1 H, br s, 19Z-H), 5.81 (1 H, d, J = 10 Hz, 7-H), 5. (5Z,7E)-(1S,3R,20S)-1,3-Bis(tert-butyldimethyl-silyl)-oxy-9,10-seco-5,7,10(19) -pregnatriene-20-carboxylic Acid Methyl Ester (4). To a stirred solution of 100 mg (0.24 mmol) of ester 15 in 10 mL of ethyl ether was added 10 mL of a 0.1 N solution of KOH in methanol. The solution was stirred at room temperature for 90 min. until no starting material was detected by TLC (hexane/ethyl acetate, 1:1). Dihydroxy ester 17 was isolated by standard extraction procedure (ethyl acetate, saturated NaCl, anhydrous MgSO$_4$) as a colorless oil (86.2 mg, 96%). A mixture of 250 mg (3.6 mmol) of imidazole and 250 mg (1.6 mmol) of tert-butyldimethylsilyl chloride in 2 mL of DMF was then added to a stirred solution of 86.2 mg (0.23 mmol) of 17 in 4 mL of DMF. The mixture was stirred for 15 min. at 55° C. until no starting material was detected by TLC (hexane/ethyl acetate, 1:1). The product was isolated with hexane. The organic extract was washed with brine and dried (MgSO$_4$). A hexane solution of the crude product was filtered through a silica gel SepPak cartridge to give 4 (136 mg, 98%) as a colorless oil: IR (film) 2974, 2930, 1736, 1447, 1286, 1258, 1150, 1085 cm-$^1$; UV (hexane) $\lambda_{max}$ 264 nm, $\lambda_{min}$ 227, A264/A227 = 1.91; $^1$H NMR (CDCl$_3$) $\delta$0.07 [12 H, s, Si(CH$_3$)$_2$]$_2$, 0.55 (3 H, s, 18-CH$_3$), 0.86 [18 H, s, C(CH$_3$)$_3$], 1.20 (3 H, d, J = 6.8 Hz, 21-CH$_3$), 3.65 (3 H, s, OCH$_3$), 4.18 (1 H, m, 3H), 4.36 (1 H, m, 1-H) 4.84 (1 H, d, J = 1.2 Hz, 19Z-H), 5.16 (1 H, d, J = 1.2 Hz, 19E-H), 5.96 (1 H, d, J = 11.2 Hz, 7-H), 6.19 (1 H, d, J = 11.2 Hz, 6-H); MS, m/z (intensities normalized to m/z 248) 602 (M+, 10), 470 (59), 413 (7), 338 (10), 248 (100).

6. (5Z,7E)-(1S,3R,20S)-1,3-Bis[(tert-butyldimethyl -silyl)-oxy]-9,10-seco-22,23-dinor-5,7,10(19)-cholatrien-24-ol (5). To a stirred solution of 136.2 (0.23 mmol) of ester 4 in 5 mL of anhydrous THF was added 25 mg (0.65 mmol) of lithium aluminum hydride under argon at 0° C. The suspension was stirred for 15 min at 0° C. and the excess reagent was decomposed by the dropwise addition of 10% H$_2$O in THF. The suspension was diluted with 10 mL of THF and the stirring was continued for an additional 15 min. at room temperature. The product was isolated by the standard extraction procedure with ethyl acetate. Silica gel Sep-Pak filtration in 10% ethyl acetate in hexane gave 5 (118.4 mg, 91%) as a colorless oil: IR (film) 3450, 2952, 2886, 1447, 1258, 1105, 1085, 834 cm$^{-1}$; UV (EtOH) $\lambda_{max}$ 264 nm, $\lambda_{min}$ 227, A264/A227 = 1.57; $^1$H NMR (CDCl$_3$) δ0.00 (12 H, s, SiCH$_3$), 0.53 (3 H, s, 18-CH$_3$), 0.85 [18H, s, SiC(CH$_3$)$_3$], 1.04(3H, d, J=6.4 Hz, 21-CH$_3$), 3.37 and 3.63 (1 H and 1 H, each m, 22CH$_2$), 4.17 (1 H, m, 3-H), 4.35 (1 H, m, 1-H), 4.84 (1 H, br s, 19Z-H), 5.16 (1 H, br s, 19E-H), 6.00 (1 H, d, J = 12.2 Hz, 7-H), 6.21 (1 H, d, J = 12.2 Hz, 6-H); MS, m/z (intensities normalized to m/z 248), 574 (M+, 17), 442 (67), 383 (11), 308 (17), 248 (100).

7. (5Z,7E)-(1S,3R,20S)-1,3-Bis[(tert-butyldimethylsilyl) -oxy]1,10-seco-22,23-dinor-5,7,10 (19)-chlolatrienol 22-p-Toluenesulfonate (6). An ice-cold solution of 42.7 mg (0.22 mmol) of p-toluenesulfonyl chloride in 50 μL of dry pyridine was added to a stirred solution of alcohol 5 at 0° C. under nitrogen. The mixture was stirred at 5° C. for 22 h and monitored by TLC. The reaction mixture was poured on ice-cold saturated aqueous NaHCO$_3$ and stirring was continued for another 30 min. The product was extracted with 1:1 (v/v) ethyl etherhexane. The organic phase was washed with saturated NaCl and dried over MgSO$_4$. Solvents were removed under reduced pressure and pyridine was removed in a stream of nitrogen. Crude product was purified by silica gel Sep-Pak filtration (5% ethyl acetate in hexane) to give pure tosylate 6 (54 mg, 98%): IR (film) 2950, 1580, 1367, 1267, 1189, 1178, 1099, 1085, 835 cm$^{-1}$; UV (hexane) $\lambda_{min}$ 236; $^1$H NMR (CDCl$_3$) δ 0.00 (12 H, s, SiCH$_3$), 0.43 (3 H, s, 18CH$_3$), 0.81 [18 H, s, SiC(CH$_3$)$_3$], 0.93 (3 H, d, J = 6.8 Hz, 2-CH$_3$), 2.40 (3 H, s, ArCH$_3$), 3.64 and 3.91 (1 H and 1 H, each m, 22-CH$_2$), 4.13 (1 H, m, 3-H), 4.31 (1 H, m, 1-H), 4.79 (1 H, br s, 19Z-H), 5.13 (1 H, br s, 19E-H), 5.94 (1 H, d, J = 12.8 Hz, 7-H), 6.17 (1 H, d, J = 12.8 Hz, 6-H), 7.43 and 7.84 (2 H and 2 H, each m, ArH); MS, m/z (intensity relative to m/z 248), 728 (6), 596 (30), 556 (7), 464 (7), 424 (44), 367 (19), 292 (23), 248 (100); exact mass calcd for C$_{41}$H$_{68}$O$_5$Si$_2$S 728.4338, found 728.4326.

8. 1α-hydroxy-homopregnacalciferol (19). The tosylate 6 (7 mg, 0.1 mmole) was dissolved in 3 mL of anhydrous ether and a large excess of LiAlH$_4$ added by cooling. The mixture was stirred under nitrogen for 16 hours at room temperature. The mixture was cooled to 0° C. and the excess LiAlH$_4$ carefully decomposed by the addition of wet ether. Additional ether was then added and the organic phase was washed with ice water and brine, dried and the ether removed. The residue was dissolved in ethyl acetate hexane mixture 1:1 and filtered through silica Sep-Pak and the solvents removed. The protected diol 18 was dissolved in anhydrous THF, and to this solution was added tetrabutylammonium fluoride in THF (0.5 mL, 1 M solution). The mixture was stirred under argon for 50 min at 50° C. Ether was then added and the organic phase was washed with saturated NaCl, and 10% NaHCO$_3$solution. Solvents were removed and the residue was dissolved in 20% 2-propanol in hexane and filtered through a silica Sep-Pak. Preparative HPLC (column 9.4 mm × 25 cm, 20% 2-propanol in hexane) gave 1-hydroxy-homopregnacalciferol (0.5 mg) identical in all respects (UV, nmr, Mass Spec) with the previously prepared compound UV(EtOH) $\lambda_{max}$ 264 nm, $\lambda_{min}$ 227 nm $^1$H NMR (CDCl$_3$)δ 0.54 (3H,s, 18-CH$_3$), 0.85 (1H, d, J = 7Hz, 22-H) 0.93 (1H, d, J = 7.0 Hz, 21-H), 4.23 (1H, m, 3-H), 4.42 (1H, m, 1-H), 5.0 (1H, s, 19(Z)-H) 5.34 (1H, s, 19(E)-H), 6.02 (1H, d, J = 12 Hz, 7-H), 6.39 (1H, d, J = 12 Hz, 6-H); MS, m/z (relative intensity), 330(M+, 55), 312(71), 287(7), 269(7), 251(5), 189(21), 152(73), 134(100).

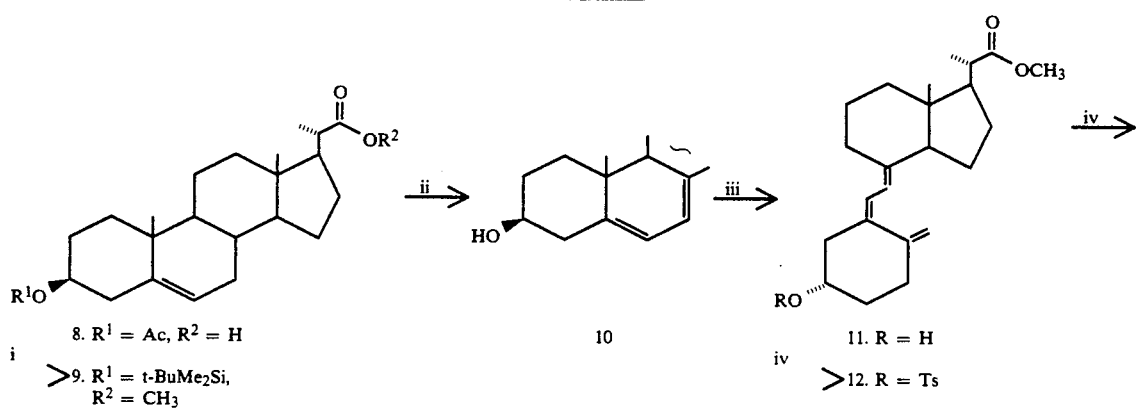

Scheme I

-continued
Scheme I

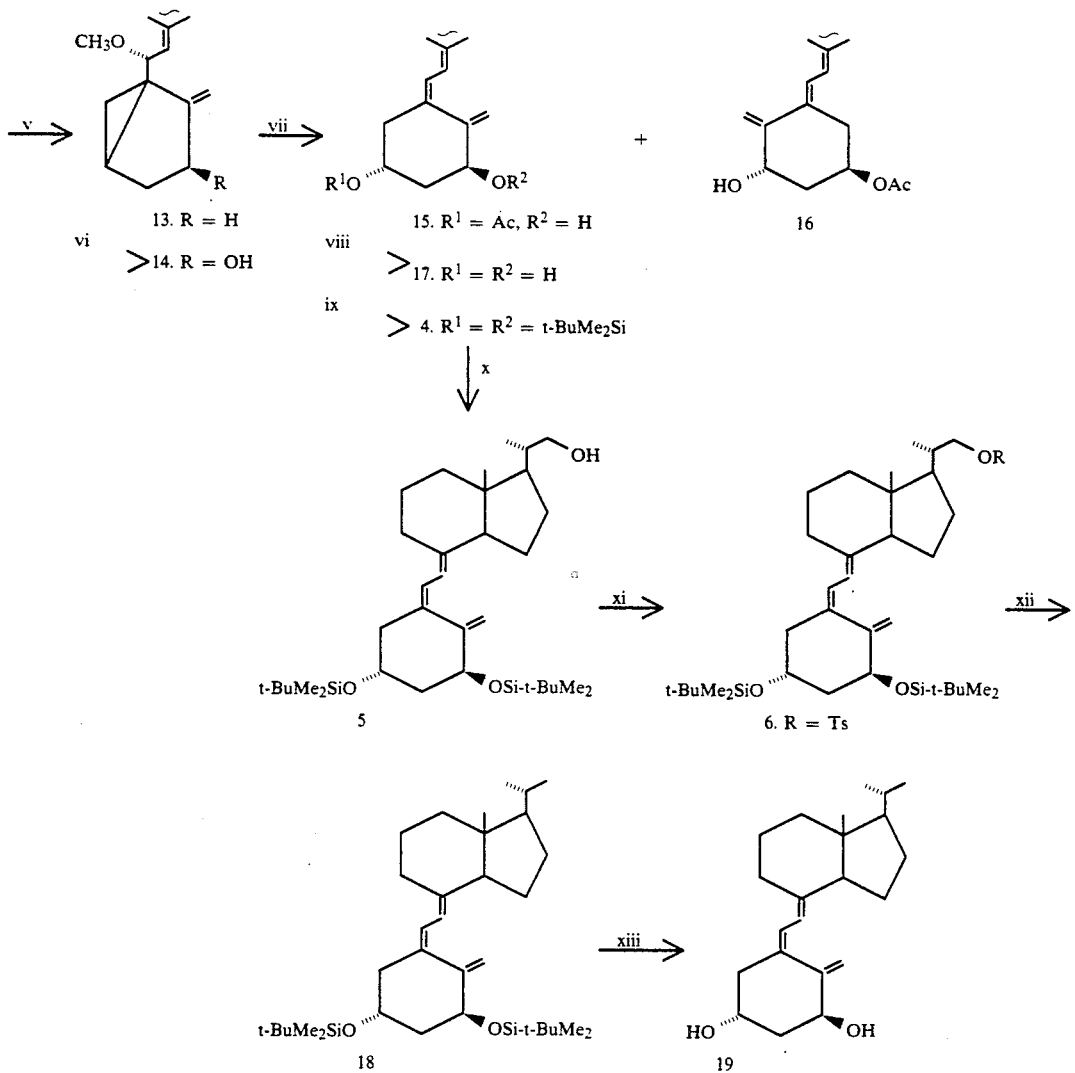

<sup>a</sup>Reagents and conditions:
(i) KOH, MeOH; H$_2$SO$_4$, MeOH; t-BuMe$_2$SiCl, imidazole, DMF;
(ii) dibromantin, KHCO$_3$, hexane, Δ; n-Bu$_4$NBr, THF; n-Bu$_4$NF, s-collidine;
(iii) hv, C$_6$H$_6$—Et$_2$O; EtOH, Δ;
(iv) p-TsCl, py, 4° C.;
(v) KHCO$_3$, MeOH, CH$_2$Cl$_2$, 55° C.;
(vi) t-BuOO, SeO$_2$CH$_2$Cl$_2$, py;
(vii) AcOH, 55° C.;
(viii) KOH, MeOH—Et$_2$O;
(ix) t-BuMe$_2$SiCl, imidazole, DMF, 55° C.;
(x) LiAlH$_4$, THF, 0° C.
(xi) p-TsCl, py, 5° C.;
(xii) LiAlH$_4$, ether, RT, 16 h
(xiii) n-Bu$_4$NF, THF, 55° C.

We claim:
1. A method of making 1α-hydroxy-secosterol compounds comprising the steps of providing a tosylate of the formula

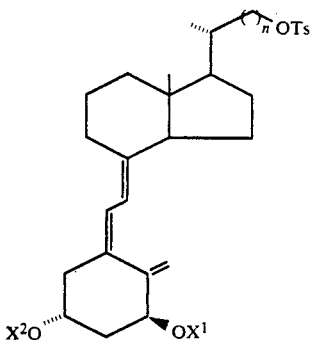

where n represents an integer having a value of 1 to 3, and $X^1$ and $X^2$ represent, independently, a hydroxy-protecting group, reducing the tosylate with LiAlH$_4$ to a 22-alkyl derivative of the formula

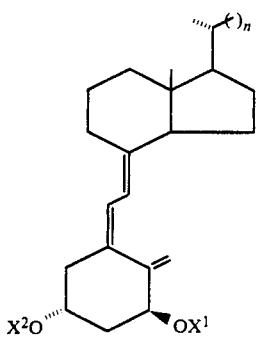

where n, $X^1$ and $X^2$ are as defined above and thereafter converting the 22-alkyl derivative to the desired 1α-hydroxy-secosterol wherein $X^1$ and $X^2$ are both hydrogen.

2. The process of claim 1 wherein prior to the converting step $X^1$ and $X^2$ are both t-BuMe$_2$Si.

3. The process of claim 1 wherein said conversion step includes the step of dissolving the 22-alkyl derivative in anhydrous THF.

4. The process of claim 3 further including the step of admixing tetrabutylammonium fluoride to the tosylate in THF solution, and thereafter heating the admixture.

5. The process of claim 1 wherein the hydroxy-protecting group is an acyl.

6. The process of claim 1 wherein the desired secosterol is 1α-hydroxy-22-methyl-pregnacalciferol.

7. The process of claim 1 wherein the desired secosterol is 1α-hydroxy-22-ethyl-pregnacalciferol.

8. The process of claim 1 wherein the desired secosterol is 1α-hydroxy-22-propyl-pregnacalciferol.

9. A method of making 1α-hydroxy-homopregnacalciferol comprising the steps of providing a 22-tosylate of the formula where $X^1$ and $X^2$ represent, independently, a hydroxy-protecting group, reducing the 22-tosylate with LiAlH$_4$ to a 22-methyl derivative of the formula where $X^1$ and $X^2$ are as defined above, and thereafter converting the 22-methyl derivative to 1α-hydroxy-homopregnacalciferol wherein $X^1$ and $X^2$ are both hydrogen.

10. The process of claim 9 wherein prior to the converting step $X^1$ and $X^2$ are both t-BuMe$_2$Si.

11. The process of claim 9 wherein said conversion step includes the step of dissolving the 22-methyl derivative in anhydrous THF.

12. The process of claim 11 further including the step of admixing tetrabutylammonium fluoride to the 22-tosylate in THF solution, and thereafter heating the admixture.

13. The process of claim 9 wherein the hydroxy-protecting group is an acyl.

* * * * *